(12) United States Patent
Tekulve

(10) Patent No.: US 8,118,817 B2
(45) Date of Patent: Feb. 21, 2012

(54) DETACHABLE EMBOLIZATION COIL

(75) Inventor: Kurt J. Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 303 days.

(21) Appl. No.: 12/506,347

(22) Filed: Jul. 21, 2009

(65) Prior Publication Data

US 2011/0022003 A1    Jan. 27, 2011

(51) Int. Cl.
*A61B 17/22* (2006.01)
(52) U.S. Cl. .......................... 606/127; 604/530
(58) Field of Classification Search ............. 606/108, 606/194, 198, 200, 127, 113, 114; 604/264, 604/530
See application file for complete search history.

(56) References Cited

U.S. PATENT DOCUMENTS

| | | | |
|---|---|---|---|
| 4,402,319 A | 9/1983 | Handa et al. | |
| 5,108,407 A * | 4/1992 | Geremia et al. | 606/108 |
| 5,725,534 A | 3/1998 | Rasmussen | |
| 6,117,157 A | 9/2000 | Tekulve | |
| 6,331,184 B1 | 12/2001 | Abrams | |
| 6,458,137 B1 | 10/2002 | Klint | |
| 6,544,225 B1 | 4/2003 | Lulo et al. | |
| 6,589,236 B2 | 7/2003 | Wheelock et al. | |
| 6,669,719 B2 | 12/2003 | Wallace et al. | |
| 6,673,058 B2 | 1/2004 | Snow | |
| 6,776,788 B1 | 8/2004 | Klint et al. | |
| 7,422,569 B2 * | 9/2008 | Wilson et al. | 604/113 |
| 2002/0161395 A1 | 10/2002 | Douk et al. | |
| 2004/0204701 A1 | 10/2004 | Cox et al. | |
| 2007/0005100 A1 | 1/2007 | Jones et al. | |
| 2007/0112420 A1 | 5/2007 | LaDuca | |
| 2008/0188884 A1 | 8/2008 | Gilson et al. | |
| 2009/0054905 A1 | 2/2009 | Levy | |

FOREIGN PATENT DOCUMENTS

| | | |
|---|---|---|
| EP | 0 832 607 A1 | 4/1998 |
| WO | WO 2007/121405 A2 | 10/2007 |
| WO | WO 2008/112435 A2 | 9/2008 |

OTHER PUBLICATIONS

S. Claiborne Johnston, et al., entitled "Recommendations for the Endovascular Treatment of Intracranial Aneurysms," http://stroke.ahajournals.org/cgi/content/full/33/10/2536, Stroke, Journal of the American Heart Association, 2002; pp. 2536-2544, published by American Heart Association in Dallas, TX.

* cited by examiner

*Primary Examiner* — Victor Nguyen
(74) *Attorney, Agent, or Firm* — Brinks Hofer Gilson & Lione

(57) ABSTRACT

An embolization delivery system and a method of using the system by a physician to deliver an embolization coil into the vasculature of a patient is disclosed. The embolization delivery system includes a delivery tube in the form of a catheter or wire guide that may be reversibly inserted, a delivery catheter placed into the vasculature of a patient, a connector disposed around and permanently coupled to the delivery tube, a detachable embolization coil disposed within a portion of the connector and held in place by compressive forces exerted by the connector, and a release mechanism for detaching the embolization coil. The release mechanism includes a wire with one end being coupled to the catheter, a middle portion being in contact with both the connector and coil, and a second end that may be manipulated in a predetermined manner by the attending physician. The manipulation of the wire splits part of the connector, thereby reducing the compressive forces exerted by the connector onto the embolization coil and allowing the coil to detach from the embolization delivery system.

15 Claims, 4 Drawing Sheets

DETACHABLE EMBOLIZATION COIL

FIELD

This invention relates generally to the field of methods and devices used for the embolization of vascular abnormalities. More specifically, this invention pertains to an embolization delivery system that includes an embolization coil and a mechanism for its detachment.

BACKGROUND

An abnormal bulge or aneurysm may occur in a body vessel due to the weakening of the vessel's wall. If the aneurysm grows large enough it may rupture and produce internal hemorrhaging, which can lead to a life threatening condition. In order to prevent rupturing, physicians have developed various methods, such as surgical clipping, and endovascular treatment. Endovascular treatment includes the use of a balloon or coil to occlude the flow of blood into the vascular abnormality by creating a physical barrier. The selection of either surgery or endovascular treatment depends upon individualized risk factors, the location of the aneurysm, the size of the aneurysm, and the likelihood of complete occlusion.

During endovascular treatment an embolization coil is typically delivered to a desired location in the vasculature of a patient through the use of a catheterization procedure. In this procedure, a catheter is inserted into the vasculature of a patient and positioned to be proximal to the desired or targeted location. Then a coil is loaded into the lumen of the catheter and advanced through the catheter using a "push" rod until it reaches and exits through the distal end of the catheter. Unfortunately, this technique suffers from difficulty associated with the precise and controlled placement of the embolization coil. Accordingly, there exists a continual desire to develop and provide a system or mechanism for the placement of an embolization coil into the vasculature of a patient that can be done in a precise and controlled manner, while maintaining overall simplicity, reliability, and manufacturability.

SUMMARY

The present invention provides an embolization delivery system and a method of using said system by a physician to deliver an embolization coil into the vasculature of a patient. One embodiment of an embolization delivery system, constructed in accordance with the teachings of the present invention, generally comprises a delivery tube, which may be either a catheter or a wire guide that may be inserted into the vasculature of a patient, a connector disposed around and permanently coupled to the delivery tube, a detachable embolization coil disposed within a portion of the connector and held in place by compressive forces exerted by the connector, and a release mechanism for detaching the embolization coil. The release mechanism includes a wire with one end being coupled to the delivery tube, a middle portion being in contact with both the connector and coil, and a second end that may be manipulated in a predetermined manner by the attending physician. The manipulation of the wire splits part of the connector, thereby, reducing the compressive forces exerted by the connector onto the embolization coil and allowing the coil to detach from the embolization delivery system.

According to another aspect of the present disclosure, the wire may coupled to the catheter or wire guide by being embedded in the surface of the connector, encased within the body of the connector, or attached by soldering, welding, brazing, adhesive bonding, or melt bonding.

According to another aspect of the present disclosure, the connector is preferably a shrink tube. The connector may be coupled to the delivery tube (i.e., catheter or wire guide) through the use of adhesive bonding, ultrasonic welding, or melt bonding. This coupling may be further assisted by the existence of frictional forces between the connector and delivery tube and by the compressive forces exerted by the connector onto the delivery tube. Overall, the coupling of the connector to the delivery tube includes an interface length of at least about $1/10^{th}$ the longitudinal length of the connector.

According to yet another aspect of the present disclosure, the length of the split in the connector made by manipulation of the wire is less than about $9/10^{th}$ the longitudinal length of the connector. Thus the connector remains attached to the catheter or wire guide after being split by the wire and can be removed from the vasculature along with the catheter/wire guide. The use of multiple wires to make multiple cuts in the connector is possible.

Another objective of the present disclosure is to provide a method of delivering an embolization coil into the vasculature of a patient. This method comprises the steps of inserting a delivery catheter into the vasculature of the patient proximal to a pre-selected target location, inserting an embolization delivery system comprising a delivery tube (i.e., another catheter or a wire guide) along with a connector, an embolization coil, and a wire release mechanism into the catheter manipulating the wire in a predetermined manner to cause it to split part of the connector and reduce the compressive forces exerted by the connector on the coil; and detaching the coil from the connector in order to complete delivery of the coil proximate to the target location.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
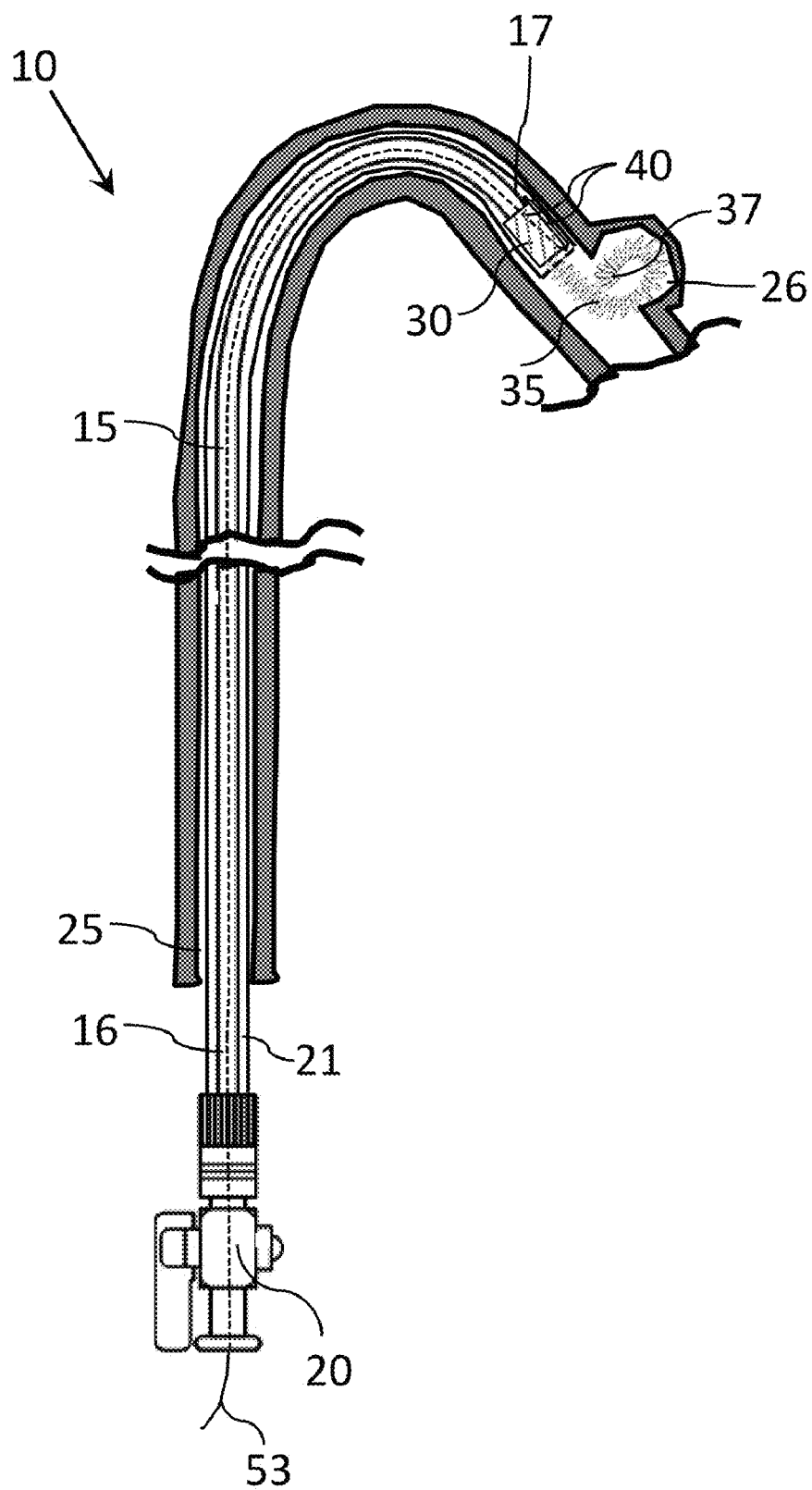
FIG. 1 is a perspective schematic of an embolization delivery system according to the teachings of the present disclosure inserted into the vasculature of a patient.

The following description is merely exemplary in nature and is in no way intended to limit the present disclosure or its application or uses. It should be understood that throughout the description and drawings, corresponding reference numerals indicate like or corresponding parts and features.

The present disclosure generally provides an embolization delivery system that may be used by a physician to deliver an embolization coil into the vasculature of a patient. Referring to FIG. 1, the embolization delivery system 10 comprises a delivery tube, such as a catheter 15 having a proximal 16 and a distal 17 end, a connector 30, a detachable embolization coil 35, and a release mechanism 40. One skilled-in-the-art will understand that the catheter 15 may be replaced by a wire guide without exceeding the scope of the present disclosure. The proximal end 16 of the catheter 15 may be coupled to or pass through any form of a manifold 20 known to one skilled-in-the-art for use with procedures that include a catheter 15 or delivery catheter 21. The embolization delivery system 10 utilizes a delivery catheter 21 to establish a pathway through the vasculature 25 of the patient. The delivery catheter 21, which may be coupled to or pass through the manifold 20, is first inserted into the vasculature 25 of the patient to a preselected or targeted location. The distal end 17 of the catheter 15 in the embolization delivery system 10 is capable of being inserted through the delivery catheter 21 into the vasculature 25 of the patient and positioned proximate to an aneurysm 26 or other abnormality in the vasculature 25.

Figure 2A:
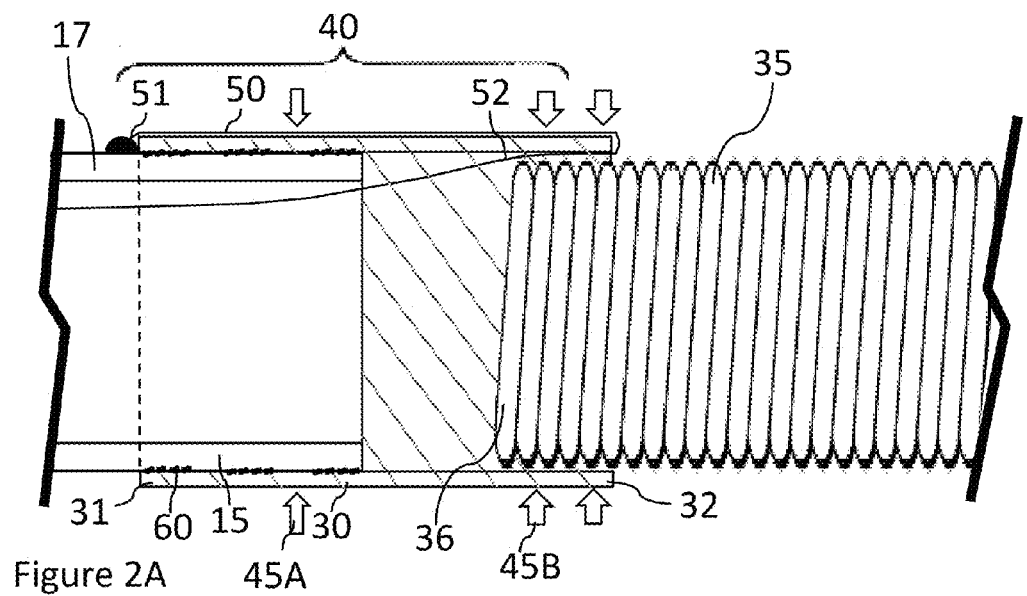
FIG. 2A is a partial cross-sectional view of the release mechanism for the embolization delivery system shown in FIG. 1.
Figure 2B:
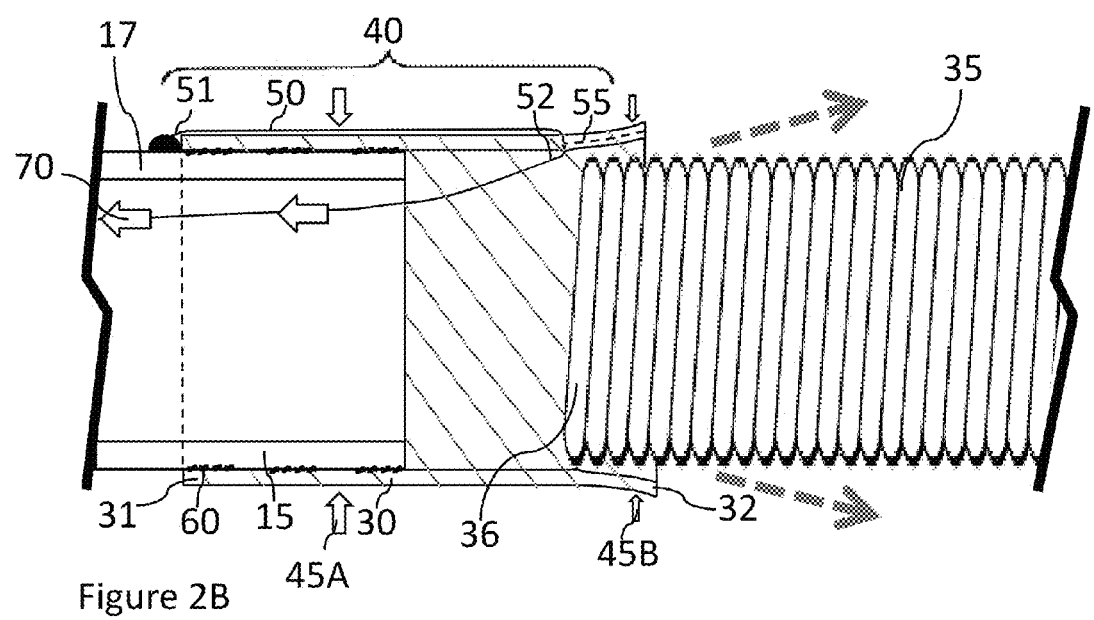
FIG. 2B is a partial cross-sectional view of the release mechanism for the embolization delivery system of FIG. 1 where a physician is manipulating the wire of the release mechanism to deploy the embolic coil.

Referring now to FIGS. 1, 2A, and 2B, the connector 30 has a proximal 31 and a distal 32 portion, while the embolization coil 35 has a proximal end 36 and a distal end 37. The proximal portion 31 of the connector 30 is disposed around and permanently coupled to the distal end 17 of the catheter 15. The proximal end 36 of the coil 35 is disposed within the distal portion 32 of the connector 30 and held in place by compressive forces 45 exerted by the connector 30.

The proximal end 36 of the embolization coil 35 is substantially straight or linear due to the boundary constraints placed upon the proximal end 36 of the coil 35 by the connector 30. The proximal end 36 of the coil 35 is securely held in place by the compressive forces 45B being placed upon the proximal end 36 of the coil 35 by the connector 30. In addition, the entire coil 35 is substantially straight or linear as it progresses through the delivery catheter 21 due to the boundary constraints placed upon the coil 35 by the delivery catheter 21. However, upon exiting the distal end of the delivery catheter 21, the distal end 37 of the embolization coil 35 will curl or coil in order to occlude the flow of fluid to the aneurysm 26 or other abnormality in the vasculature 25.

The release mechanism 40 for detaching the embolization coil 35 comprises a wire 50 that has a first end 51, a middle portion 52, and a second end 53. The first end 51 of the wire 50 is coupled to the distal end 17 of the catheter 15, while the middle portion 52 of the wire 50 is in contact with the distal portion 32 of the connector 30 and the proximal end 36 of the coil 35 and travels through the catheter 15 in the direction of the catheter's proximal end 16. The second end 53 of the wire 50 goes beyond the proximal end 16 of the catheter 15 so that it may be manipulated in a predetermined manner by the attending physician.

The connector 30 may be coupled to the catheter 15 through the use of any known method of bonding 60 including but not limited to the use of adhesives ultrasonic welding, or melt bonding. In addition, frictional forces exerted between the connector 30 and catheter 15, as well as compressive forces 45A exerted by the connector 30 onto the catheter 15 may assist in securing the connector 30 to the catheter 15. One skilled-in-the-art will understand that the length of the interface between the connector 30 and catheter 15 needs to be such that the connector 30 is securely coupled to the catheter 15. Preferably, at least about $1/10^{th}$ or more of the longitudinal length of the connector 30 is coupled to the catheter 15.

The first end 51 of the wire 50 incorporated as part of the release mechanism 40 may be coupled to the distal end 17 of the catheter 15 using one selected from the group of soldering, welding, brazing, adhesives bonding, and melt bonding, as well as any other attachment mechanism known to one skilled-in-the-art. The middle portion 52 of the wire extends from the first end 51 along the external surface of the connector 30 and over the distal portion 32 of the connector into the lumen established by the connector 30 and the catheter 15. The middle portion 52 of the wire 50 may contact the proximal end 36 of the embolization coil 35. The placement of the middle portion 52 of the wire around the distal portion 32 of the connector 30 may be facilitated by a groove or notch etched into the distal portion 32 of the connector 30. The middle portion 52 of the wire 50 extends through the lumen of the catheter 15. The second end 53 of the wire 50 may extend beyond the proximal end 16 of the catheter 15 and manifold 20 in order to be accessible for manipulation by a physician or other attendant.

Referring to FIG. 2B, the manipulation 70 of the second end 52 of the wire 50 splits a portion 55 of the connector 30, thereby, reducing or eliminating the compressive forces 45B exerted by the connector 30 onto the proximal end 36 of the embolization coil 35, thereby, allowing the coil 35 to detach from the embolization delivery system. Typically this manipulation 70 will involve the pulling or moving the wire 50 in a manner that causes the middle portion 52 of the wire 50, which is in contact with the distal portion 32 of the connector 30 to cut into or through the connector 30. This cut 55 reduces the compressive forces 45B exerted by the connector 30 onto the proximal end 36 of the embolization coil 35. The length of the cut 55 made by the wire 50 into or through the connector 30 will vary depending upon the extent to which the physician manipulates the wire 50 through its proximal end 53 and to the degree over which the compressive forces 45B need to be reduced. The length of the cut 55 is determined by the magnitude of the applied compressive forces 45B applied by the connector 30 and the associated decrease in these forces 45B that will allow the coil 35 to be released into the vasculature.

The wire 50 may cut 55 the connector 30 up to the point at which the connector 30 is coupled to the catheter 15. Thus the connector 30 remains coupled to the catheter 15 even after the cut 55 has been made. This allows the connector 30 to be removed from the vasculature when the catheter 15 is removed. Preferably, the cut 55 is less than about $9/10^{th}$ of the longitudinal length of the connector 30.

According to another aspect of the present disclosure, multiple cuts 55 may be made in the connector 30 when desirable through the use of a plurality of wires 50 in the release mechanism 40. Although one skilled-in-the-art will understand that any number of wires 50 may be used in the release mechanism 40, in order to maintain the ease of manufacturing and simplicity of operation less than about seven wires 50 would be desirable. When more than one wire 50 is utilized, it is possible that each of the wires 50 may be attached to one another in the middle portion 52 of each wire that travels through the lumen of the catheter 15. Such attachment may be accomplished by any means of fastening including but not limited to tying, weaving, and bonding.

Figure 3A:
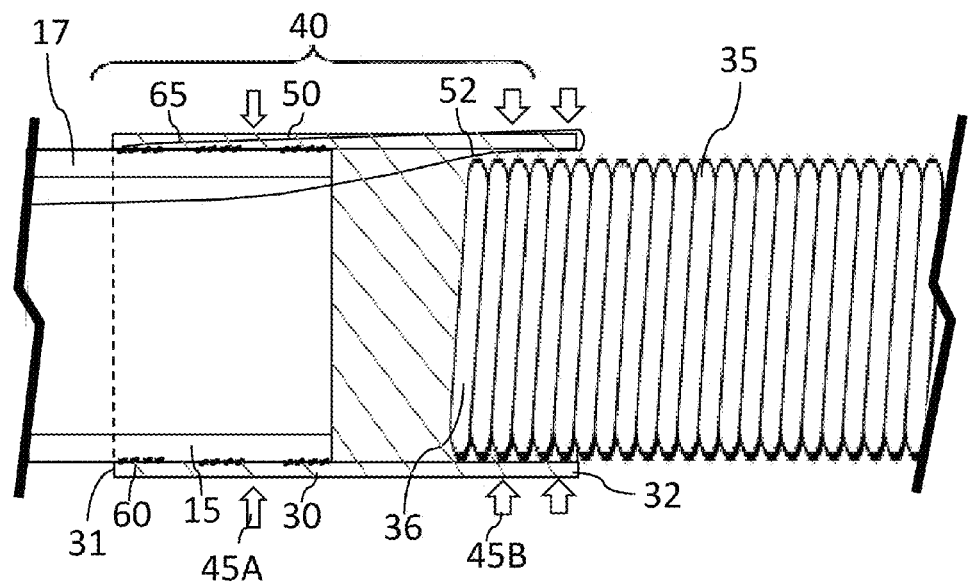
FIG. 3A is a partial cross-sectional view of the release mechanism for the embolization delivery system of FIG. 1 according to another aspect of the present disclosure.

Referring now to FIG. 3A, according to another aspect of the present disclosure, the wire 50 may be coupled to the connector 30 by embedding the first end 65 of the wire 50 either into the surface of the connector 30 or encased within the body of the connector 30. In this situation, the middle portion 52 of the wire 50 will still be positioned on the external surface of the connector 30 at the point at which is it goes around the distal end 32 of the connector 30 into the lumen established by the connector 30 and catheter 15.

Figure 3B:
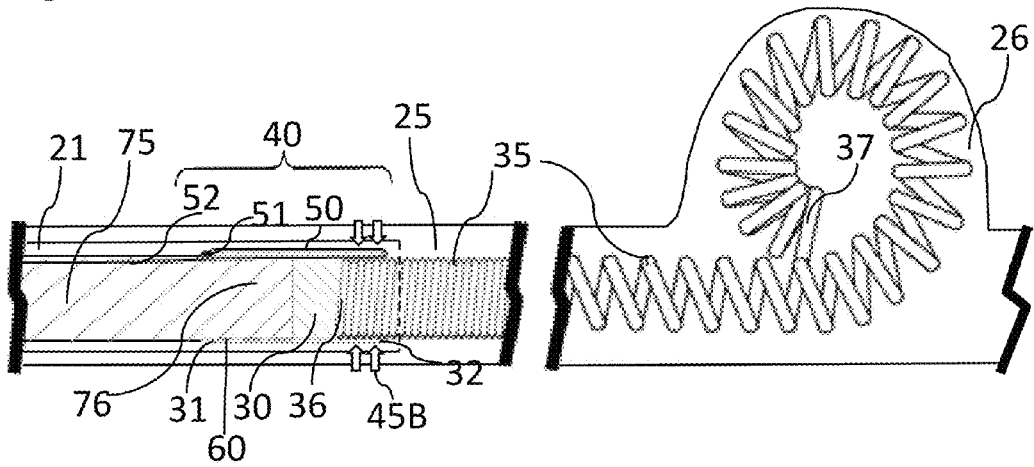
FIG. 3B is a partial cross-sectional view of the distal portion of an embolization delivery system according to another aspect of the present disclosure.

Referring now to FIG. 3B, an embolization delivery system 10 wherein a wire guide 75 is used in place of a catheter 15 as the delivery tube is depicted. According to this aspect of the present disclosure, the connector 30 may be coupled to the distal end 76 of a wire guide 75. This connector 30 securely holds the proximal end 36 of the embolization coil 35 in a substantially linear geometry. The embolization delivery system 10 including the wire guide 75 is configured to utilize a delivery catheter 21 as a means through which the embolization delivery system 10 is positioned proximate to the aneurysm 26 in the vasculature 25 of the patient. The first end 51 of the wire 50 may be coupled to the distal end 76 of the wire guide 75.

The middle portion 52 of the wire extends from the first end 51 along the external surface of the connector 30 and over the distal portion 32 of the connector into a space established between the connector 30 and the wire guide 75. The middle portion 52 of the wire 50 may contact the proximal end 36 of the embolization coil 35. The placement of the middle portion 52 of the wire around the distal portion 32 of the connector 30 may be facilitated by a groove or notch etched into the distal portion 32 of the connector 30. The middle portion 52 of the wire 50 extends along the length of the wire guide 75 and through the lumen of the delivery catheter 21. The second end 53 of the wire 50 may extend beyond the proximal end of the delivery catheter 21 in order to be accessible for manipulation by a physician or other attendant.

The connector 30 may be made of one selected from the group of polyethylene terphthalate (PET), polyvinyl chloride (PVC), a polyolefin, fluoropolymers, such as polytetrafluoroethylene (PTFE), polyimides, polyamides, polyurethanes, and a combination thereof. Preferably the connector 30 is a "shrink tube" selected to fit over the distal end of the delivery tube (e.g., catheter 15 or wire guide 75) and the proximal end of the embolization coil 35 and then shrunk by the application of heat to apply a compressive force against the coil, thereby, holding the coil in place. The external surface of the connector may include a hydrophilic coating to enhance lubricity. The wall thickness of the connector may range from about 0.03 mm to about 0.2 mm.

The delivery tube, i.e., the catheter 15 or wire guide 75, may be made of any material known to one skilled-in-the-art, including but not limited to woven Dacron®, polyvinylchloride, polyurethane, polytetrafluoroethylene (PTFE), silicone, and nylon, as well as various metals and metal alloys, such as steel and Nitinol. The diameter of the delivery tube typically may be in the range of about 1 to about 9 French units with 1 French unit being equivalent to about ⅓ mm.

The wire 50 in the release mechanism 40 may be comprised of any metal, metal alloy, or composite that is harder than the material used in making the connector 30 and that has a break strength or yield stress that exceeds the level necessary to make a cut 55 in the connector 30. Examples of metals and metal alloys include stainless steel, nickel-cobalt, Nitinol, platinum, iridium, gold, and combinations thereof. The diameter of the wire 50 may range from about 0.04 mm to about 0.4 mm. One skilled-in-the-art will understand that the strength of the wire 50 is selected based upon the composition, thickness, and properties exhibited by the connector 30.

The embolization coil 35 may be made from a metal or metal alloy selected as one from the group of platinum, stainless steel, iridium, palladium, tungsten, gold, Nitinol, and combinations or mixtures thereof. The metal or metal alloy is selected to minimize or limit the potential for surface contamination and preferably is substantially free of any surface oxidation. Optionally, the embolization coil 35 may include a radiopaque or echogenic feature to assist in locating the coil proximate to the abnormality in the vasculature through the use of x-ray fluoroscopy or sonography.

The embolization coil 35 may be any shape known to one skilled-in-the-art, including but not limited to helical and conical shapes. The embolization coil 35 may also include synthetic, thrombogenic fibers located proximate to the multiple radially expanding, tightly spaced turns in the coil. The embolization coil, as well as any thrombogenic fibers may include a coating that incorporates a therapeutic agent, such as collagen, heparin, methotrexate, or forskolin among others.

The embolization coil 35 may be of any desired length or size determined to be necessary to function as desired. Typically, the embolization coil is made from a wire having a diameter in the range of about 0.054 to 0.3 mm. The embolization coil 35 will typically exhibit a coiled embolus diameter in the range of about 2-20 mm and an extended embolus length in the range of about 2 to 30 cm.

Upon splitting the connector 30, the reduction in compressive forces exerted by the connector 30 on the embolization coil 35 allows the coil to separate itself from the connector and become deployed within the vasculature 25 of the patient. It is also foreseeable that pressure applied through the lumen of the catheter 21 may be used to assist in overcoming the resistance of blood flow within the vasculature, thereby, further facilitating the separation of the embolization coil 35 from the connector 30. The application of pressure through a catheter 21 may arise by any method known to one skilled-in-the-art, including the injection of a liquid (i.e., saline flush). Optionally, the movement of the delivery tube (e.g., catheter 15 or guide wire 75) may be used to facilitate separation.

Figure 4:
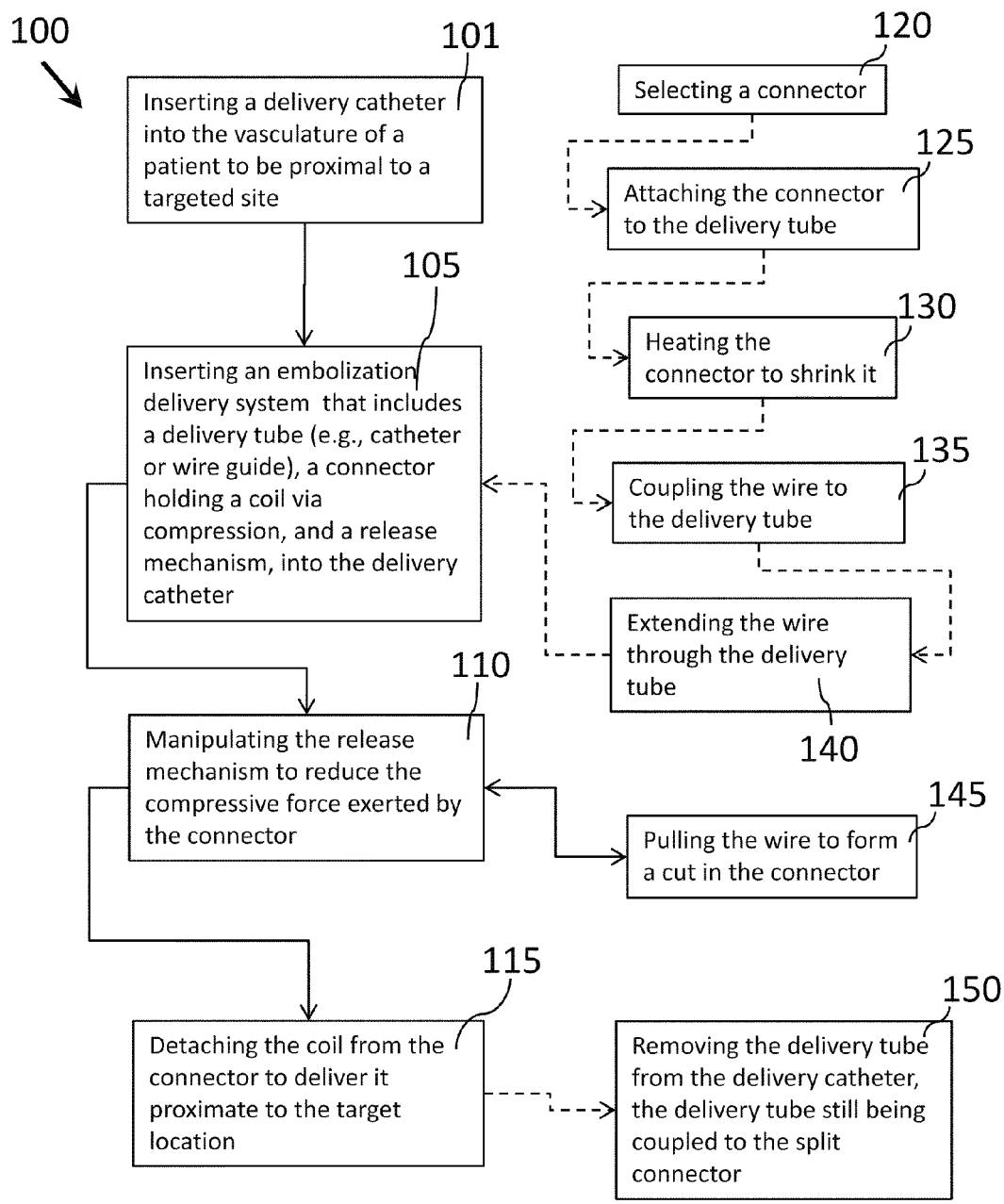
FIG. 4 is a flowchart describing a method of delivering an embolization coil into the vasculature of a patient according to one embodiment of the present disclosure.

Referring now to FIG. 4, it is another objective of the present disclosure to provide a method 100 of delivering an embolization coil into the vasculature of a patient. The method 100 comprises the steps of inserting a delivery catheter into the vasculature of a patient to be proximal to a pre-selected targeted site, inserting 105 an embolization delivery system into the delivery catheter, manipulating 110 a release mechanism in a predetermined manner to reduce or release the compressive forces that hold the embolization coil in the embolization delivery system, and detaching 115 the coil from the embolization delivery system to deliver it proximate to the desired or targeted location.

This method 100 uses the embolization delivery system 10 as previously described in the present disclosure. More specifically, the embolization delivery system 10 comprises a delivery tube, such as a catheter 15 or wire guide 75, a connector 30 disposed around and permanently coupled to the delivery tube; a detachable embolization coil 35 disposed within the connector 30 and held in place by compressive forces 45 exerted by the connector 30; and a release mechanism 40 for detaching the embolization coil 35, the mechanism comprising a wire 50 with a first end 51 coupled to the delivery tube, a middle portion 52 in contact with the connector 30 and the coil 35, and a second end 53. The manipulation of the second end 53 of the wire 50 by a physician in a predetermined manner causes the middle portion 52 of the wire 53 to split part of the connector 30 in order to reduce the compressive forces 45 exerted by the connector 30 on the coil 35.

The method 100 may further comprise the steps of selecting 120 a connector 30 having the wall thickness and strength necessary to provide a compressive force 45 against an embolization coil 35 in order to hold the coil 35 in place; attaching 125 the connector 30 to a delivery tube (e.g., catheter 15 or wire guide 75), heating 130 the connector 30 in order to shrink it and apply the desired compressive force 45 against the coil 35; and coupling 135 the first end 51 of the wire 50 to the distal end 17 of the catheter 15 or wire guide 75. The middle portion 52 of the wire 50 is allowed 140 to extend through the lumen of the catheter 15 or along the length of the wire guide 75 with its proximal end 53 being located near or outside the proximal end of the catheter 21 and manifold 20 making it easily accessible to a physician or other attendant.

The predetermined manner in which the wire 50 is manipulated includes pulling 145 the wire 50 to cause its middle portion 52 to form a cut 55 in the distal portion 32 of the connector 30, thereby, reducing the compressive forces 45 exerted by the connector 30 onto the embolization coil 35. After releasing the embolization coil 35 proximate to the desired or targeted location, the catheter 15 or wire guide 75 including the split connector 30, which is still attached to the distal end of the catheter 15 or wire guide 75, may be removed 150 from the vasculature.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An embolization delivery system used by a physician to deliver an embolization coil into the vasculature of a patient; the embolization delivery system comprising:
    a delivery catheter inserted into the vasculature of the patient;
    a delivery tube having a proximal end and a distal end, the delivery tube selected as one from the group of a catheter and a wire guide, the distal end of the delivery tube capable of being inserted into the delivery catheter;
    a connector having a proximal portion and a distal portion; the proximal portion being disposed around and permanently coupled to the distal end of the delivery tube;
    a detachable embolization coil having a distal end and a proximal end; the proximal end of the coil being disposed within the distal portion of the connector and held in place by compressive forces exerted by the connector; and
    a release mechanism for detaching the embolization coil, the mechanism comprising a wire having a first end, a middle portion, and a second end, the first end being coupled to the distal end of the delivery tube, the middle portion being in contact with the distal portion of the connector and the proximal end of the coil; the wire positioned so that its second end may be manipulated in a predetermined manner by the physician through the proximal end of the delivery catheter;
    wherein manipulation of the second end of the wire causes the middle portion to split part of the connector, thereby, reducing the compressive forces exerted by the connector onto the embolization coil and allowing the coil to detach from the embolization delivery system.

2. The embolization delivery system of claim 1, wherein the first end of the wire is coupled to the delivery tube by being embedded in the surface of the connector.

3. The embolization delivery system of claim 1, wherein the first end of the wire is coupled to the delivery tube by one selected from the group of soldering, welding, brazing, adhesive bonding, and melt bonding.

4. The embolization delivery system of claim 1, wherein the connector is comprised of one selected from the group of polyethylene terphthalate (PET), polyvinyl chloride (PVC), a polyolefin, fluoropolymers, such as polytetrafluoroethylene (PTFE), polyimides, polyamides, polyurethanes, and a combination thereof.

5. The embolization delivery system of claim 4, wherein the connector is a shrink tube.

6. The embolization delivery system of claim 1, wherein the connector is coupled to the delivery tube through the use of one selected from the group of adhesive bonding, ultrasonic welding, or melt bonding.

7. The embolization delivery system of claim 6, wherein the coupling of the connector to the delivery tube is assisted by frictional forces between the connector and delivery tube and by compressive forces exerted by the connector onto the delivery tube.

8. The embolization delivery system of claim 1, wherein the coupling of the connector to the delivery tube includes an interface length of at least about $1/10$th the longitudinal length of the connector.

9. The embolization delivery system of claim 1, wherein the length of the split in the connector made by manipulation of the wire is less than about $9/10$th the longitudinal length of the connector.

10. The embolization delivery system of claim 9, wherein the connector remains attached to the delivery tube after being split by the wire.

11. The embolization delivery system of claim 1, wherein the release mechanism comprises more than one wire, each wire positioned to split the connector upon manipulation of the wire in a predetermined manner.

12. A method of delivering an embolization coil into the vasculature of a patient, the method comprising the steps of:
    inserting a delivery catheter into the vasculature of a patient to a location that is proximate to a pre-selected targeted site;
    inserting an embolization delivery system into the delivery catheter, the embolization delivery system comprising a delivery tube, a connector disposed around and permanently coupled to the delivery tube; a detachable embolization coil disposed within the connector and held in place by compressive forces exerted by the connector; and a release mechanism for detaching the embolization coil, the mechanism comprising a wire with a first end coupled to the delivery tube, a middle portion in contact with the connector and the coil, and a second end;
    manipulating the second end of the wire in a predetermined manner to cause the middle portion of the wire to split part of the connector and reduce the compressive forces exerted by the connector on the coil; and
    detaching the coil from the connector in order to complete delivery of the coil proximate to the target location.

13. The method of claim 12, wherein the method further comprises the steps of:
    selecting a connector, the connector having the wall thickness and strength necessary to provide a compressive force that can hold the embolization coil in place;

attaching the connector to the delivery tube, the delivery tube selected as one from the group a catheter and a wire guide;

heating the connector in order to shrink it and apply the desired compressive force against the coil; and coupling the first end of the wire to the delivery tube.

14. The method of claim 12, wherein the predetermined method of manipulating the wire includes pulling the wire to cause its middle portion to form a cut in the connector.

15. The method of claim 12, the method further comprising the step of removing the delivery tube from the vasculature, the delivery tube still being coupled to the connector after the connector has been split.

* * * * *